US005609162A

United States Patent [19]
Blumentritt et al.

[11] Patent Number: 5,609,162
[45] Date of Patent: Mar. 11, 1997

[54] DISPLAY SYSTEM FOR PROJECTING THE CENTER OF GRAVITY OF THE HUMAN BODY

[75] Inventors: Siegmar Blumentritt; Thomas Brendel, both of Duderstadt; Steffen Sawatzki, Sollestedt, all of Germany; Paul G. van de Veen, Enschede, Netherlands

[73] Assignee: Otto Bock Orthopadische Industrie Besitz-und-Verwaltungs-Kommanditgesellschaft, Duderstadt, Germany

[21] Appl. No.: 372,114

[22] Filed: Jan. 13, 1995

[30] Foreign Application Priority Data

Jan. 15, 1994 [DE] Germany .................. 44 01 036.2

[51] Int. Cl.$^6$ ............................................. A61B 5/103
[52] U.S. Cl. ................................................ 128/782
[58] Field of Search ............................. 128/774, 782, 128/714; 356/373

[56] References Cited

U.S. PATENT DOCUMENTS

| 3,712,294 | 1/1973 | Muller | 128/782 |
| 3,890,958 | 6/1975 | Fister et al. | 128/714 |
| 4,598,717 | 7/1986 | Pedotti | 128/779 |
| 4,819,660 | 4/1989 | Smith | 128/774 |

FOREIGN PATENT DOCUMENTS 2121688  1/1984  United Kingdom ............. A61B 5/10

OTHER PUBLICATIONS

Lord, M., et al., "Video aid to rehabilitation of standing balance", Medical & Biological Engineering & Computing, May 1982, pp. 281–285.

*Primary Examiner*—Max Hindenburg
*Assistant Examiner*—Pamela Wingood
*Attorney, Agent, or Firm*—Whitham, Curtis, Whitham & McGinn

[57] ABSTRACT

The invention relates to a center of gravity control display system for measuring the human body and/or prosthetic or orthotic fittings in their positions relative to the human body. According to the invention, this system consists of a measuring plate (1) for determining center of gravity (4) projected in the plane of measuring plate (1), of a person standing on measuring plate (1), and of a projection device (2) for projecting a perpendicular measuring line onto the body of said person, with measuring plate (1) being provided with pressure sensors (3) connected with one another by a circuit, said sensors delivering an electrical signal defining the determined center of gravity position, said signal controlling a drive that displaces an optical system in a plane parallel to that of measuring plate (1), said system projecting a light beam (19) as a vertical measuring line that defines a plane in which center of gravity (4) of the person being measured lies.

25 Claims, 3 Drawing Sheets

DISPLAY SYSTEM FOR PROJECTING THE CENTER OF GRAVITY OF THE HUMAN BODY

BACKGROUND OF THE INVENTION

1. Field of the Invention

The invention relates to a display system controlled by the center of gravity, for measuring the human body and/or prosthetic and orthotic fittings in their positions relative to the human body.

2. Description of the Prior Art

A prosthesis or orthosis that is optimally designed in terms of all the activities of a prosthesis wearer is not feasible. Thus for example a prosthesis optimally designed for walking is not optimal as a rule for the prosthesis wearer when seated. However, since walking is the most important function, as a rule an attempt is made when devising an optimum prosthesis to investigate other functions such as standing, sitting, or lying down, in order possibly to make changes in the design of the prosthesis.

The center of gravity line of the human body as it relates to the joint positions plays an important role in the measurement of the body.

SUMMARY OF THE INVENTION

The goal of the invention is to develop a display system with which the body's center of gravity line can be represented visually, quickly, and exactly.

This goal is achieved according to the invention by a display system consisting of a measuring plate for determining the center of gravity, projected in the plane of this measuring plate, of a person standing on the measuring plate, and of a projection device for projecting a perpendicular measuring line onto the body of this person, with the measuring plate being equipped with pressure sensors connected with one another by a circuit, said sensors delivering an electrical signal that defines the center of gravity position thus determined, said circuit controlling a drive that displaces an optical system in a plane parallel to that of the measuring plate, said system projecting a light beam as a perpendicular measuring line that defines a plane in which the center of gravity of the measured person lies.

With this display system, the vertical body center of gravity line in the sagittal and/or frontal plane can be projected onto the body, with, this center of gravity line lying exactly on the plane that passes through the body's center of gravity at the outset of the measurement. In the corresponding initial position, the light beam follows the movements of the body's center of gravity with an accuracy of $\leq \pm 2$ mm.

In addition to this basic projection, the display system also allows measurement of the distance between this center of gravity line and special points on the body to be measured or on a prosthetic or orthotic device (for example the position of a joint with respect to the body's center of gravity axis.

Basically, it is also possible to display the weight of the person being measured by means of the measuring plate.

According to the invention it is advantageous for the drive to be a stepping motor. In order to move small weights in the projection device, it is advantageous for the stepping motor to be mounted in a stationary position. The display system according to the invention therefore requires only relatively low electrical power.

A projection device that is simple in design and operates precisely is then ensured in which a stepping motor drives an endless toothed belt connected to a carriage bearing the optical system. This produces a design whose structure is especially simple for the projection device when the projection device has a straight carriage guide, at both ends of which a housing is provided, one of said housings containing the stepping motor with the drive wheel for the toothed belt and the other housing containing the counterbearing for returning the toothed belt.

The light beam can preferably be a laser beam.

In a first alternative solution it is advantageous for the laser emitting the laser beam to be mounted in a stationary fashion and for the optical system to have a linearally guided deflecting mirror. The deflecting mirror is preferably mounted on a carriage guided on a carriage guide. In order to be able to project a vertical measuring line on the body to be measured using the deflected laser beam, it is advantageous for the deflecting mirror to be rotatable around an axis located parallel to its direction of displacement. Advantageously, a motor mounted on the carriage is provided for this purpose, on whose drive shaft the deflecting mirror is mounted.

In a second alternative solution, provision is made according to the invention such that the light source emitting the light beam is mounted on a carriage guided on a carriage guide. The light source is preferably a laser with reticle optics. In this design, no deflecting mirror with its drive is required.

Preferably a honeycomb material is provided as the top for the measuring plate according to the invention. It is possible, especially because of the resultant flexibility, to make the measuring plate in one piece according to the invention.

Additional features of the invention are the subjects of the subclaims and will be explained in greater detail with additional advantages of the invention on the basis of an embodiment.

DESCRIPTION OF THE DRAWINGS

The drawings show an embodiment of the invention in schematic form intended as an example.

Figure 1:
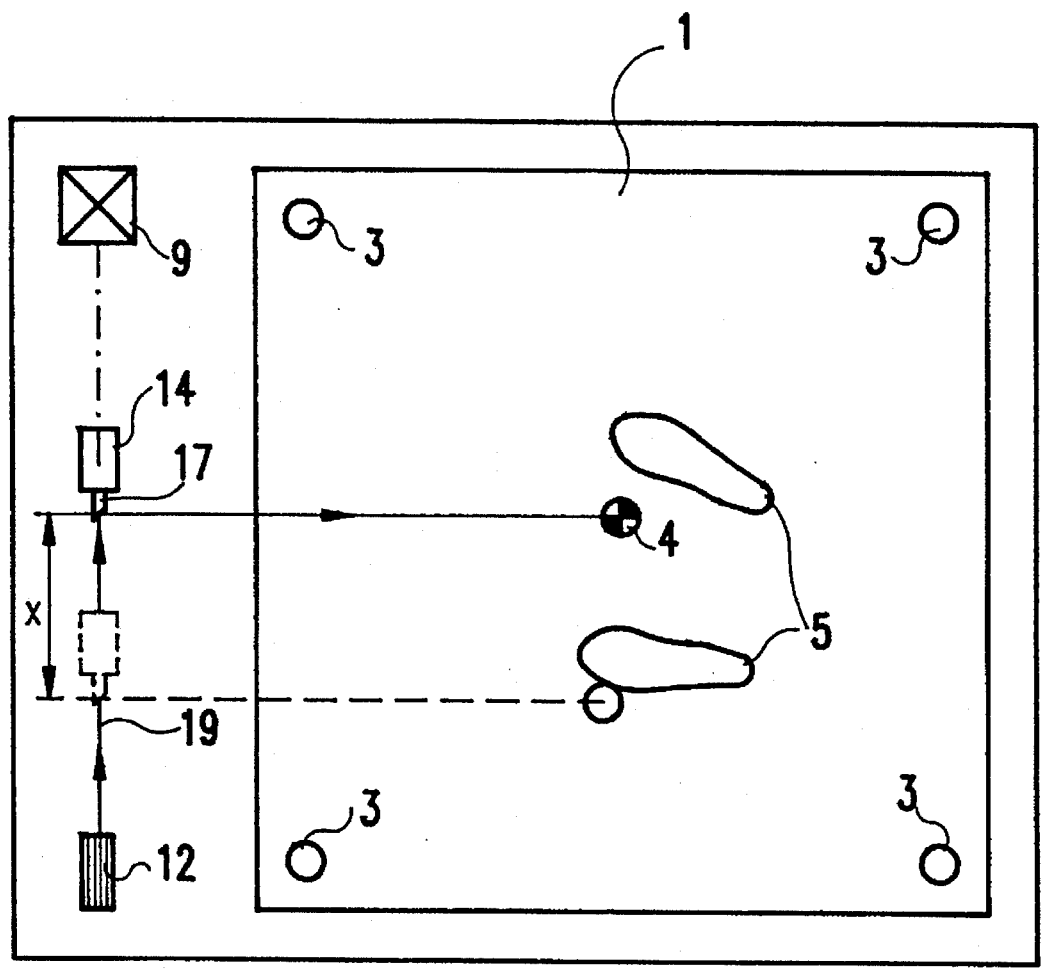
FIG. 1 is a top view of a display system consisting of a projection device and a measuring plate.
Figure 2:
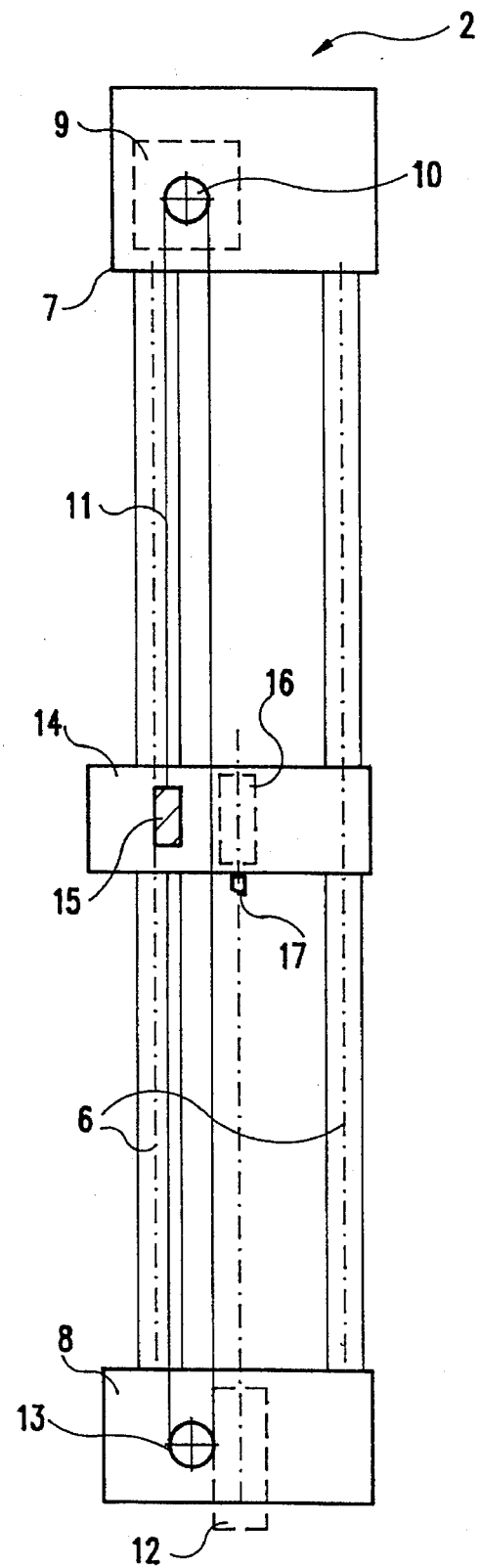
FIG. 2 shows the projection device on an enlarged scale in a top view.
Figure 3:
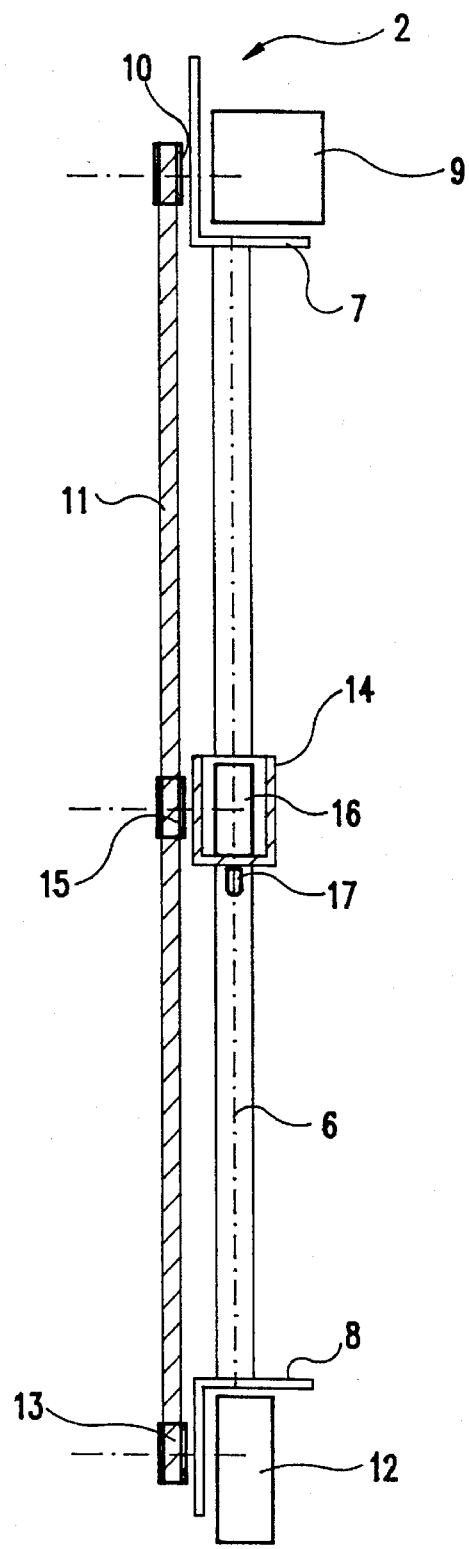
FIG. 3 is the view shown in FIG. 2 in a side view and partially in cross section.

The display system shown in FIG. 1 in highly schematic form comprises a measuring plate 1 as well as a projection device 2 that are preferably combined with one another to form a unit. The adjustment of projection device 2 relative to measuring plate 1 is not variable; in addition, the display system can be operated very simply.

DESCRIPTION OF THE PREFERRED EMBODIMENT

Measuring plate 1 is made in one piece and consists mainly of honeycomb material, and has at least four pressure sensors 3, preferably located at the corners of measuring plate 1, said sensors being transducers connected with one another by a circuit not shown in greater detail in the drawing. With the aid of this sensor circuit, the center of gravity 4 of a person standing on measuring plate 1 (only the two feet 2 are shown schematically in FIG. 1) can be determined in its position within the plane formed by measuring plate 1.

Projection device 2 consists mainly of a straight carriage guide 6 with a housing 7,8 at each end. One housing 7 encloses a stepping motor 9 with a drive wheel 10 for an endless toothed belt 11, while the other housing 8 accommodates a laser 12 as well as counterbearing 13 for returning toothed belt 11. A carriage 14 is mounted displaceably on carriage guide 6, said carriage being couplable by a clamping device 15 or the like with toothed belt 11 and bearing a motor 16 on whose driveshaft a deflecting mirror 17 is mounted. Motor 16 is arranged so that deflecting mirror 17 is rotatable parallel to the displacement direction of carriage 14 or around an axis 18 lying parallel to carriage guide 6.

Laser 12 emits a light beam 19 which, as shown in FIG. 1, strikes deflecting mirror 17 and is deflected by the latter at right angles in the direction of measuring plate 1. By rotation of deflecting mirror 17, a perpendicular plane can be spanned by light beam 19. However, since linear projection of this plane onto the person to be measured is all that is really required, it is advantageous to provide a reversible rotary drive for deflecting mirror 17 with a rotational angle of only 60° for example.

Pressure sensors 3 that determine the position of center of gravity 4 of a person standing on measuring plate 1 and to be measured deliver an electrical signal that corresponds to the position of center of gravity 4 on the x axis plotted in FIG. 1. Stepping motor 9 receives this electrical signal and displaces carriage 14 into the x position by means of toothed belt 11 in which deflected light beam 19 or the perpendicular plane defined thereby assume the same x position as the determined center of gravity 4, which then comes to rest in the plane spanned by light beam 19 that is in the form of a vertical measuring line on the person to be measured. In order now to be able to determine the exact x-distance of an articulation point, device or the like from this center of gravity plane, by manual control of stepping motor 9 of carriage 14, the perpendicular measuring line generated by deflecting mirror 17 on the person to be measured is displaced by a distance $x_1$ until this perpendicular measuring line intersects the point to be measured. Distance $x_1$ can be displayed digitally for example, so that the respective distance measurements can be made by only one operator quickly, simply, and exactly.

We claim:

1. Display system controlled by the center of gravity, for measuring the human body and/or prosthetic and orthotic fittings in their position relative to the human body, comprising:

a measuring plate for determining the center of gravity, projected in the plane of said measuring plate, of a person standing on said measuring plate, a projection device arranged outside said measuring plate and comprising an optical system for projecting a light beam defining a vertical measuring line and a drive for displacing said optical system in a plane parallel to that of said measuring plate, said measuring plate being provided with pressure sensors connected with another via a circuit, said sensors delivering an electrical signal defining the position of the center of gravity thus determined, said electrical signal controlling said drive for displacing said optical system to a terminal position in which the projected vertical measuring line and the center of gravity of the measured person lying within the same vertical plane.

2. Display system according to claim 1 characterized in that the drive is a stepping motor.

3. Display system according to claim 2 characterized in that said stepping motor is mounted stationary.

4. Display system according to claim 3 characterized in that said stepping motor drives an endless toothed belt connected with a carriage supporting the optical system.

5. Display system according to claim 4 characterized in that said projection device comprises a straight carriage guide and a housing at each end of said carriage guide, one housing accommodating said stepping motor with the drive wheel for said toothed belt, and the other housing accommodating a counterbearing for returning said toothed belt.

6. Display system according to claim 1 characterized in that the optical system can be moved under manual control, by respectively defined distances.

7. Display system according to claim 1 characterized in that said light beam is a laser beam.

8. Display system according to claim 7 characterized in that the laser emitting the laser beam is mounted stationary and the optical system has a linearly guided deflecting mirror.

9. Display system according to claim 8 characterized in that said deflecting mirror is mounted on a carriage, said carriage guided on said carriage guide.

10. Display system according to claim 8 characterized in that said deflecting mirror is rotatable around an axis parallel to its displacement direction.

11. Display system according to claim 10 characterized by a motor drive for rotating said deflecting mirror.

12. Display system according to claim 11 characterized in that said carriage comprises a motor on whose drive shaft said deflecting mirror is mounted.

13. Display system according to claim 1 characterized in that the light source emitting said light beam is mounted on a carriage, said carriage being guided on said carriage guide.

14. Display system according to claim 13 characterized in that the light source is a laser with reticle optics.

15. Display system according to claim 1 characterized in that said measuring plate is made in one piece.

16. Display system according to claim 15 characterized in that said measuring plate consists essentially of a honeycomb material.

17. Display system according to claim 1 characterized in that said projection device and said measuring plate are combined with one another to form a unit.

18. A display system, comprising:

means for determining a center of gravity of a person or object in a first plane;

means for projecting a measuring line on said person or object, said measuring line being perpendicular to said first plane; and means for displacing said means for projecting said measuring line; in response to said means for determining center of gravity, whereby said measuring line can be projected on a desired location of said person or object by said means for projecting.

19. The display system of claim 18, wherein said means for determining includes:

a support on which said person or object is positionable;

a plurality of transducers connected to said support; and a circuit connected to said plurality of transducers, said circuit producing an electrical signal which defines the position of said center of gravity.

20. The display system of claim 19 wherein said electrical signal is supplied to said means for displacing said means for projecting said measuring line.

21. The display system of claim 18 wherein said means for projecting a measuring line includes a laser and wherein said means for displacing said means for projecting said measuring line includes a mirror positioned in line with a laser beam produced by said laser to reflect said laser beam towards said person or object.

22. The display system of claim 18 wherein said means for displacing displaces said means for projecting said measuring line on a second plane which parallel to said first plane.

23. The display system of claim 18 wherein said means for displacing said means for projecting said measuring line comprises:

a carriage, said means for projecting said measuring line being positioned on said carriage;

a track along which said carriage is movable; and a means for moving said carriage along said track.

24. The display system of claim 23 wherein said means for projecting said measuring line comprises a mirror positioned to reflect a laser beam directed parallel to said track towards said person or object.

25. The display system of claim 18 further comprising means for directing said means for displacing to displace said means for projecting to at least two different locations with respect to said person or object.

* * * * *